(12) United States Patent
Gonzalez-Hernandez

(10) Patent No.: US 8,343,152 B2
(45) Date of Patent: Jan. 1, 2013

(54) FIXED ANGLE DUAL PRONG PIN FIXATION SYSTEM

(75) Inventor: Eduardo Gonzalez-Hernandez, Coconut Grove, FL (US)

(73) Assignee: Toby Orthopaedics, Inc., Coral Gables, FL (US)

( * ) Notice: Subject to any disclaimer, the term of this patent is extended or adjusted under 35 U.S.C. 154(b) by 0 days.

(21) Appl. No.: 13/439,734

(22) Filed: Apr. 4, 2012

(65) Prior Publication Data
US 2012/0197310 A1   Aug. 2, 2012

Related U.S. Application Data

(63) Continuation of application No. 12/537,596, filed on Aug. 7, 2009.

(60) Provisional application No. 61/086,822, filed on Aug. 7, 2008.

(51) Int. Cl.
*A61B 17/56* (2006.01)
*A61B 17/58* (2006.01)
*A61F 2/30* (2006.01)

(52) U.S. Cl. .......................... 606/62; 606/329

(58) Field of Classification Search ............ 606/62, 606/329
See application file for complete search history.

(56) References Cited

U.S. PATENT DOCUMENTS

| | | | |
|---|---|---|---|
| 4,838,254 A * | 6/1989 | Gauthier | 606/75 |
| 5,196,014 A | 3/1993 | Lin | |
| 5,374,268 A | 12/1994 | Sander | |
| 5,520,688 A | 5/1996 | Lin | |
| 5,574,268 A | 11/1996 | Herman et al. | |
| 5,607,428 A | 3/1997 | Lin | |
| 5,709,682 A | 1/1998 | Medoff | |
| 5,941,878 A | 8/1999 | Medoff | |
| 6,203,545 B1 * | 3/2001 | Stoffella | 606/74 |
| 6,235,033 B1 | 5/2001 | Brace et al. | |
| 6,248,109 B1 | 6/2001 | Stoffella | |
| 6,368,319 B1 | 4/2002 | Schaefer | |
| RE39,035 E | 3/2006 | Finn et al. | |
| 7,744,629 B2 | 6/2010 | Hestad et al. | |
| 2006/0217719 A1 | 9/2006 | Albert et al. | |
| 2006/0247624 A1 | 11/2006 | Banouskou et al. | |
| 2008/0009867 A1 | 1/2008 | Banouskou et al. | |
| 2008/0114359 A1 | 5/2008 | Murner et al. | |
| 2008/0177262 A1 | 7/2008 | Augoyard et al. | |
| 2008/0195096 A1 | 8/2008 | Frei | |
| 2008/0262545 A1 | 10/2008 | Simonson | |
| 2010/0179602 A1 | 7/2010 | Dauster et al. | |
| 2011/0009912 A1 | 1/2011 | Gonzalez-Hernandez | |
| 2012/0004690 A1 | 1/2012 | Gonzalez-Hernandez | |

* cited by examiner

*Primary Examiner* — Andrew Yang
(74) *Attorney, Agent, or Firm* — Martin & Ferraro, LLP

(57) ABSTRACT

A bone fixation system and method are provided. The system includes a dual prong pin and a bone screw. The pin is especially configured and contoured to fixate fractures of the proximal phalanx, especially hyperextension fractures. Fracture of other long bones of the hand, foot or elsewhere may be managed with this bone fixation system.

24 Claims, 12 Drawing Sheets

FIXED ANGLE DUAL PRONG PIN FIXATION SYSTEM

The present application is a continuation of U.S. application Ser. No. 12/537,596, filed Aug. 7, 2009; which claims the benefit of U.S. Provisional Application No. 61/086,822, filed on Aug. 7, 2008; all of which are incorporated by reference herein.

BACKGROUND OF THE INVENTION

1. Field of the Invention

A bone fixation system and method suitable, for example, for fracture fixation of the proximal phalanx of the hand or foot, especially of the hyperextension type, are provided. The system is also suitable for fixating fractures of other long bones of the hand, such as the middle phalanx or the metacarpals, and of the metatarsals in the foot. The system is also suitable for fixating fractures in other bones outside of the hand or foot.

2. Description of the Prior Art

Hyperextension fractures of the proximal phalanx are typically problematic, especially in the elderly, because such fractures are very difficult to stabilize. Current techniques and devices can often lead to very significant functional impairment and disability. These hyperextension fractures of the proximal phalanx usually result in less optimal outcomes than fractures of larger bones such as the distal radius.

One of the most common methods for fracture fixation is pinning. In general, a pin has a sharp cutting tip. The pin is driven into bone with the aide of a drill or an equivalent mechanical device. Despite their versatility, pins have limitations especially with fractures that have a significant amount of fragmentation (comminution) of the bone at the fracture site or when the fractured bone is too soft resulting in premature loosening of the pins.

Another common method for fracture fixation of the small bones of the hand utilizes plate fixation. However, use of plates usually results in scaring which frequently limits the proper gliding motion of the surrounding tendons, especially the extensor tendon. A second surgery is usually necessary to remove the plate and release the extensor tendon. This approach often results in a large scar in the most visible part of the hand (not readily received by most female patients). In the presence of significant comminution and osteoporosis, as is often the case scenario in the elderly female population with these fractures, plate fixation of hyperextension fractures of the proximal phalanx is usually not able to hold the alignment of the fracture because the plate has limited mechanical ability to buttress these fractures and loss of reduction is often frequent after plate fixation.

In addition, conventional plating of the long bones of the hand frequently results in malalignment of the involved bone after the plate is applied; the operated finger will tend to abnormally scissor or overlap onto an adjacent finger. Thus, plating requires absolute precision because even a small amount of angular malalignment is not well tolerated.

Yet another fixation method utilizes a flexible nail/pin mated to a locking sleeve. This method offers some advantages over plating and pinning of the long bones of the hand. However, the nail and sleeve configuration is not much different from pins and has limited ability to control hyperextension fractures of the proximal phalanx which frequently results in loss of fracture reduction. In addition, a significant portion of the hardware is prominent outside of the bone, irritating the tendons. Some relief is provided by use of a protective plastic cap. In most cases, a second surgery is needed to remove the nail and the prominent locking sleeve.

SUMMARY OF THE INVENTION

In accordance with the principles embodying the invention, a system and method for bone fixation are provided in the form of a two prong buttress pin system. In its basic form, the system has two components—a two prong or dual prong pin and one or more bone screws, e.g., locking screws. The threads of the screw are designed to mate with the dimensions of a locking domain of the two prong pin.

The two prong pin is suitably contoured to work as a buttress. Such contouring is especially suitable in fixating hyperextension fractures of the proximal phalanx, but may also be used for fixating other bones of the hand, foot or elsewhere. The dual prong pin is also advantageous in addressing the most common flexion deformity of metacarpal fractures. Because of the contoured nature of the pin in accordance with principles embodying the invention, four points of fixation are achieved, two in the proximal fracture fragment and two in the distal fracture fragment.

The two prong pin can be used by itself or with its one or more bone screws. The bone screw, e.g., locking screw, is constructed and configured to mate to the locking domain of the pin. To facilitate insertion, a drill guide can be mated to the locking domain of the two prong device to drill the precise direction for the locking screw. A drill guide may be desirable but is not necessary because the system is very accommodating.

In an illustrated embodiment, the two prong device has a single locking domain to which a single bone screw may be mated. In another embodiment, the dual prong pin may have two locking domains to which two bones screw may be mated. More complex configurations can be devised for accommodating more than one screw or to provide an additional buttress in between the locking domains to provide additional fixation and buttress support.

In another embodiment, the two prong pin has a retaining feature configuration located on the distal portion of the prongs. This retaining configuration can take the form of raised rings or protrusions or barbs on the shank of the prongs. These configuration variations help increase the gripping power of the prongs, thus preventing separation of the fracture.

Specifically, a bone pin in accordance with the principles embodying the invention includes a substantially U-shaped member having a central region, a first prong extending from the central region and a second prong extending from the central region, spaced apart and opposite and parallel from the first prong. The central region is configured to receive and mate with one or more bone screws.

A bone fixation system in accordance with embodiments of the invention includes a bone pin and one or more bone screws. The pin is substantially U-shaped and has a central region, a first prong extending from the central region and a second prong extending from the central region, opposite and parallel to the first prong. The central region is configured to receive and mate with the bone screws. The central region lies in a transverse plane. The one or more screws each have an elongate shaft, and when mated within the central region, the shaft is substantially perpendicular to the plane of the central region.

A method and kit for fixating bone fractures are also provided.

Other advantages and a better appreciation of the specific adaptations, variations, and physical attributes of the inven-

DETAILED DESCRIPTION OF THE PREFERRED EMBODIMENT

Figure 1:
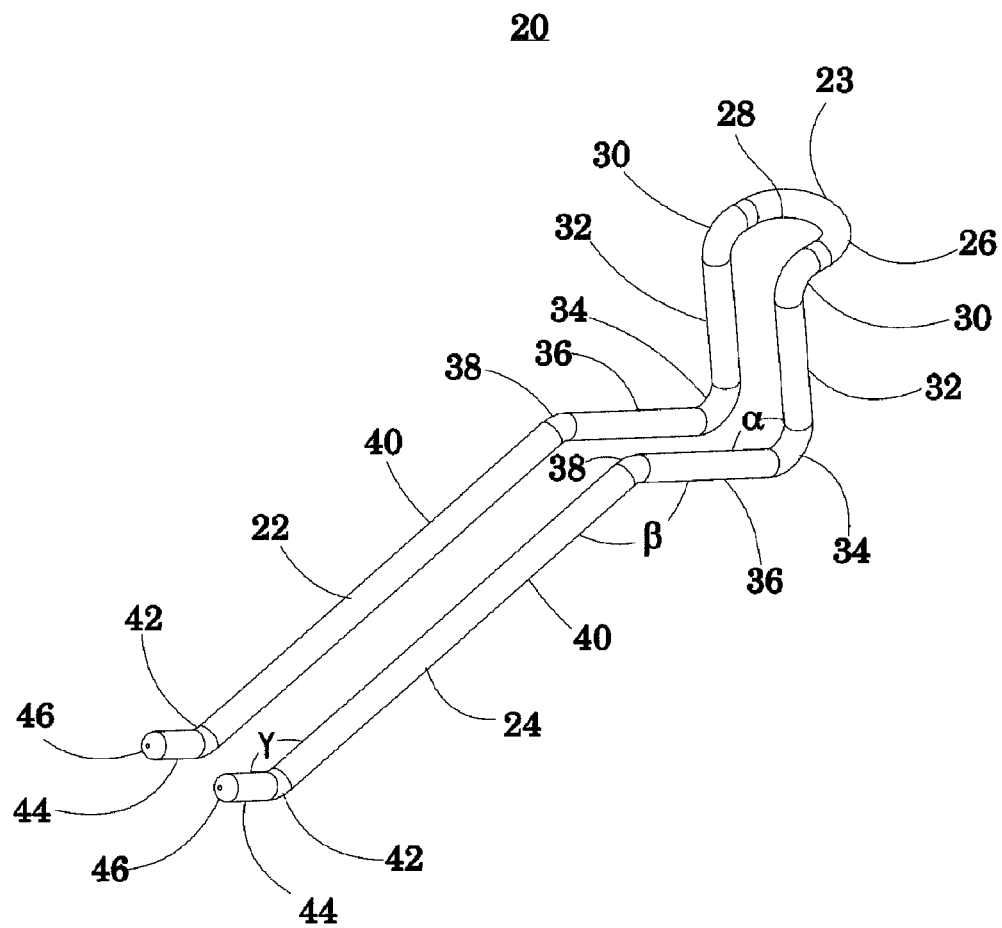
FIG. 1 illustrates a perspective view of a bone pin in accordance with the invention having a dual prong configuration and a single locking domain.

A bone fixation system embodying the principles of the invention is provided. The system includes a fixed angle dual prong bone pin and one or more bone screws, e.g., locking screws. The system acts as a buttress to resist against the main deforming forces acting on fractures, especially, for example, of the proximal phalanx, such as those acting on hyperextension fractures. The system is also well-suited for fixating fractures of other long bones in the hand, such as the metacarpals and phalanges, and long bones in the foot, such as metatarsals. Fractures of other bones of the body may also be fixated with device and method described herein.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

No admission is made that any reference, including any patent or patent document, citied in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

As used herein, the term "substantially" in reference to a shape or direction, for example, "substantially U-shaped," is meant to refer to a general or overall shape or direction. For "substantially U-shaped," it is understood, for example, that the legs of the U may vary, e.g., the legs of a U may be equal in length or unequal. The legs may also be curved or angled.

The terms "transverse plane" and "sagittal plane" are meant to refer to the conventional planes used in describing a human body, i.e., the sagittal plane travels along the Y-axis and the transverse plane is in the horizontal plane perpendicular to the sagittal plane.

The term "arcuate" is meant to describe a structure or a portion of a structure as being curved or rounded. It is understood that more than one arcuate portion may be present in a structure.

In view of the foregoing disadvantages inherent in conventional bone fixation systems, the invention provides a novel system and method for fixating bone fractures, for example, proximal phalanx fractures. Given that many fractures have not only transverse fracture components but also oblique or even rather frequently long fracture lines along the bone, it has been found advantageous for pin placement with a dual shaft/prong pin in accordance with principles of the invention.

Figure 3:
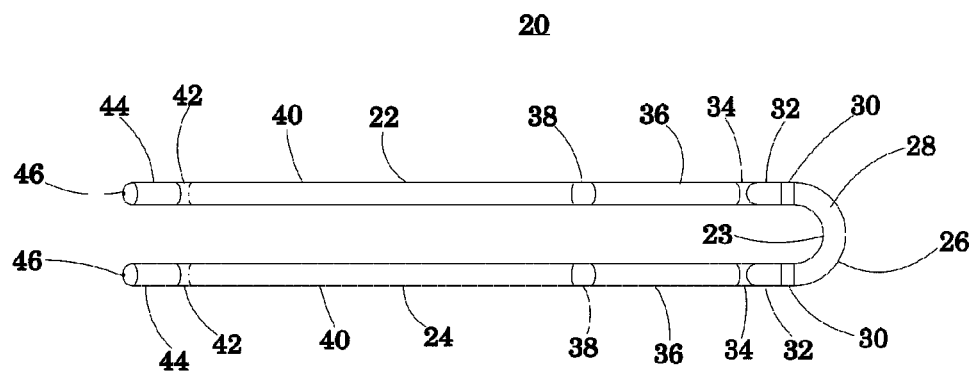
FIG. 3 illustrates a top plan view of a bone pin having a single locking domain dual prong configuration.
Figure 2:
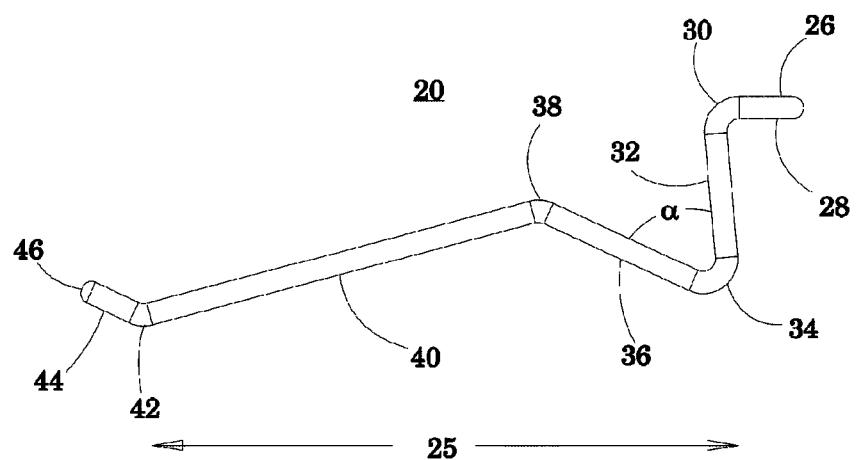
FIG. 2 illustrates a side plan view of a bone pin having a single locking domain dual prong configuration.

In one aspect, the invention provides a bone pin with a fixed angle dual prong or dual shaft configuration, and having screw locking domains. Specifically, the pin is substantially U-shaped, as seen in FIG. 3, having a central region, a first prong extending from the central region and a second prong extending from the central region, opposite and parallel to the first prong. The prongs of the pin are pre-contoured, the exact shape of which depends on the particular application. The central region lies in a transverse plane which is perpendicular to the sagittal planes of the contoured prongs.

The central region may have one or more screw locking domains to receive and mate with a bone screw, e.g., a locking screw. The locking domains of the pin are suitably one or more arcuate portions, e.g., a loop or looped portion. In use, for example, a locking bone screw is suitably mated in the locking domain. The one or more screws each have an elongate shaft, and when positioned and mated in the central region, i.e., the locking domain, e.g., the loop, the shaft is generally perpendicular to the (transverse) plane of the central region, i.e., the shaft lies in the sagittal plane.

The direction of the screw placement in the looped portion depends on the optimal configuration for individual fracture fixation and is not limited as in the existing prior art devices. In some embodiments, the bone pin according to principles of the invention may have more than one screw locking domain. The domains may be suitably positioned side by side, laterally or linearly. The locking screw has bone threads that are designed to match and mate with the features in the locking domain of the two pronged pre-contoured pin.

The full mechanical advantage of the fixed angle dual prong pin configuration in accordance with embodiments of the invention is realized when the bone screw is mated to the arcuate locking domain. For example, in embodiments in which the locking domain is a loop, the head of the screw to be mated to the loop suitably has a head to allow the diameter of the loop to mate with the minor diameter of the threaded portion of the screw proximal end. Having two fixed angle dual prongs oriented in identical directions into the substance of the bone enhances the separation strength of the pin from the bone far beyond that of a single shaft pin oriented in a similar direction.

The bone pin in accordance with principles of the invention is desirable in multiple fracture scenarios, and especially in fractures of the bones of the hand or foot, for example, the metacarpals and the phalanges. The bone fixation system is simple to insert, has a very low profile, and minimizes tendon irritation.

The dual prong configuration offers multiple mechanical advantages over a single flexible nail. For example, the bone pin according to principles of the invention has better rotational control, lower profile, improved buttressing effect, and there is no need for a secondary surgery. The system also has many advantages over plating systems. For example, embodiments of the bone pin improve buttressing of hyperextension fractures of the proximal phalanx, a lower profile, and, unlike the plate, there is no need for a secondary surgery to remove the device or to free the scarred tendon resulting in no large scar. In addition, any malrotation is easily corrected with the present two prong device.

Figure 4:
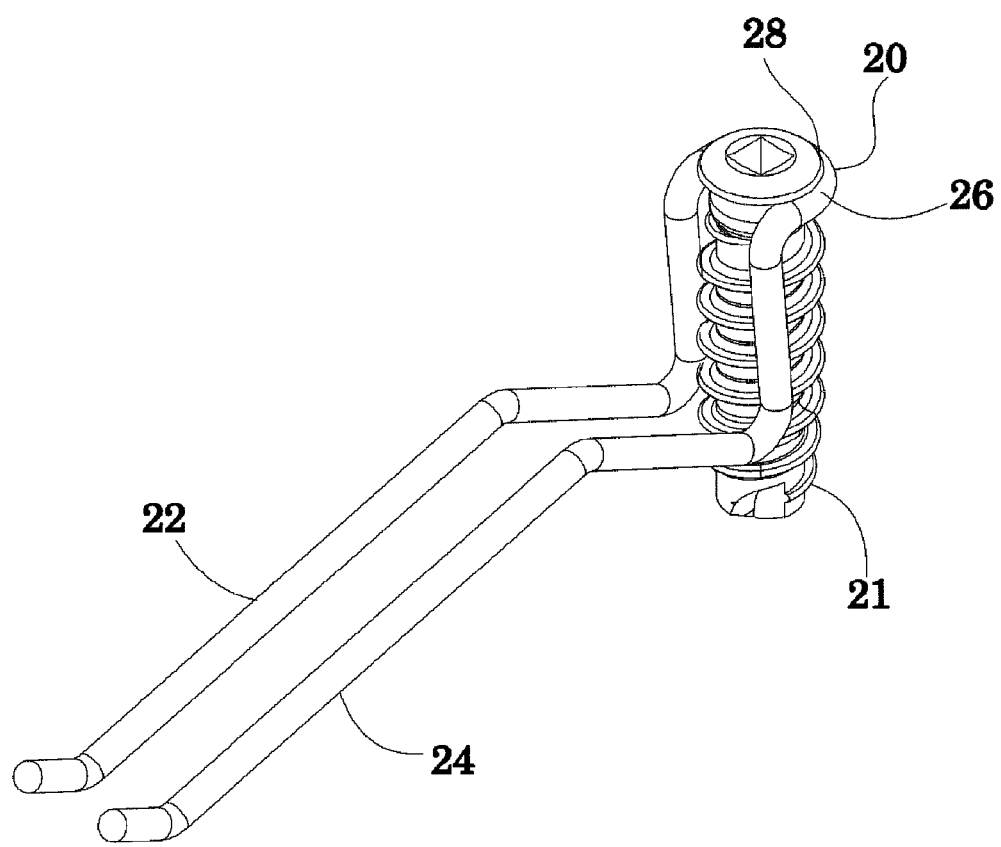
FIG. 4 illustrates a perspective view of a bone pin of FIG. 1 with a locking cortical screw engagingly mating the locking domain.

Reference is now made to FIGS. 1-4 in which a bone fixation system, generally designated by reference numeral 10, in accordance with embodiments of the invention is shown. System 10 includes a dual prong pin 20 and a screw system 21 (e.g., as seen in FIG. 4) for stabilizing bone segments. In an illustrated embodiment, dual prong pin 20 is generally overall U-shaped (as shown in FIG. 3), defined by a central region 23, a first prong 22 extending from central region 23, and a second prong 24, extending from central region 23, that is spaced apart and generally parallel to first prong 22. Central region 23 includes one or more screw locking domains 26 to receive and hold bone screws. Domains 26 are suitably one or more arcuate portions, e.g., suitably, a loop 28, as shown, e.g., in FIG. 1. Loop 28 has a predefined shape and size. Dual prong pin 20 may be provided with any size of loop 28 as may be suitable for a specific surgical application.

Dual prong pin 20 in accordance with the principles embodying the invention may have many shapes. As shown in the embodiment of FIG. 1, prongs 22, 24 are pre-contoured and suitably have a generally arched shape 25 with, e.g., an arched section aiding to grip the bone inner surface. In the embodiments illustrated in FIGS. 1-4, generally arched shape 25 of prongs 22 and 24 includes, in the sagittal plane, a first bend or arcuate portion 30 connected to a first linear portion 32 connected to a second bend or arcuate portion 34. Bend 34 is connected to a second linear portion 36 which is at an acute angle .alpha. to linear portion 32. Linear portion 36 is connected to a third bend or arcuate portion 38 connected to a third linear portion 40. Linear portion 40 is at an oblique angle .beta. to linear portion 36. Linear portion 40 is connected to a fourth bend or arcuate portion 42 and ending in a fourth linear portion 44 angled with respect to linear portion 40 at an angle .gamma. and has a terminus 46. As seen in FIG. 3, the overall configuration of pin 20 is U-shaped. As described, the arched shape coupled with the fixed angle combination enables a buttress pin configuration.

Figure 5:
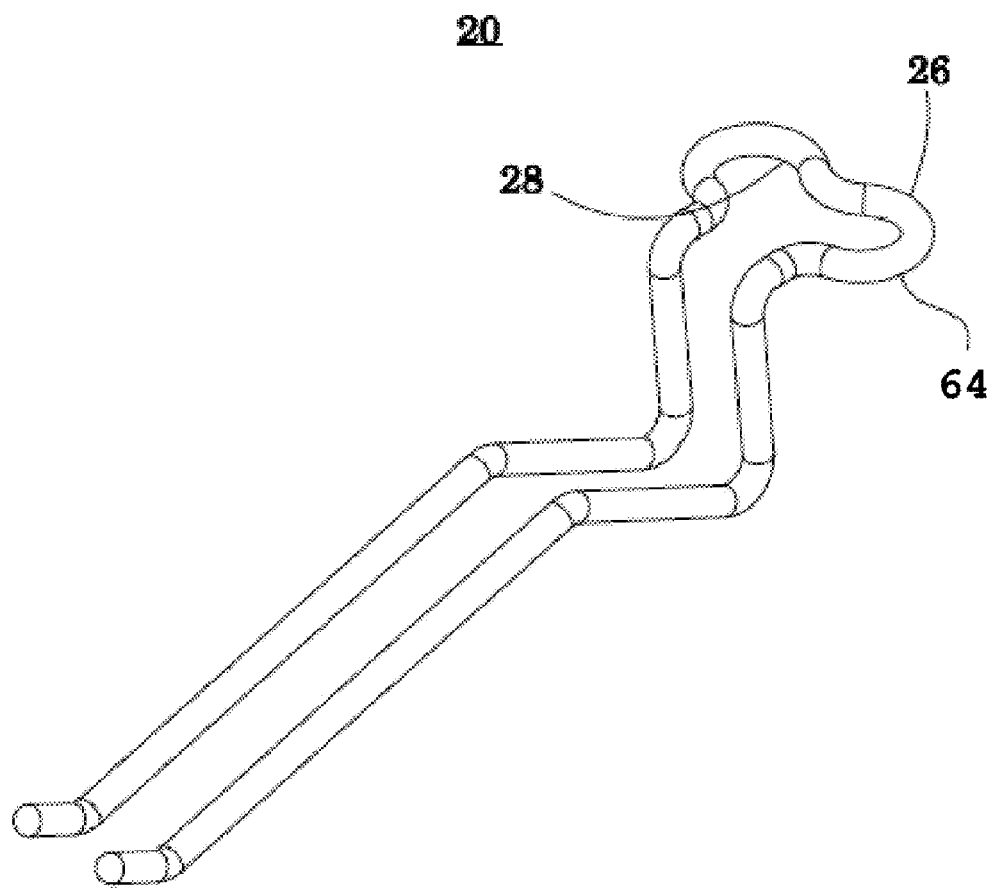
FIG. 5 illustrates a perspective view of an embodiment of a bone pin having dual lateral locking domains and a dual prong configuration.
Figure 6:
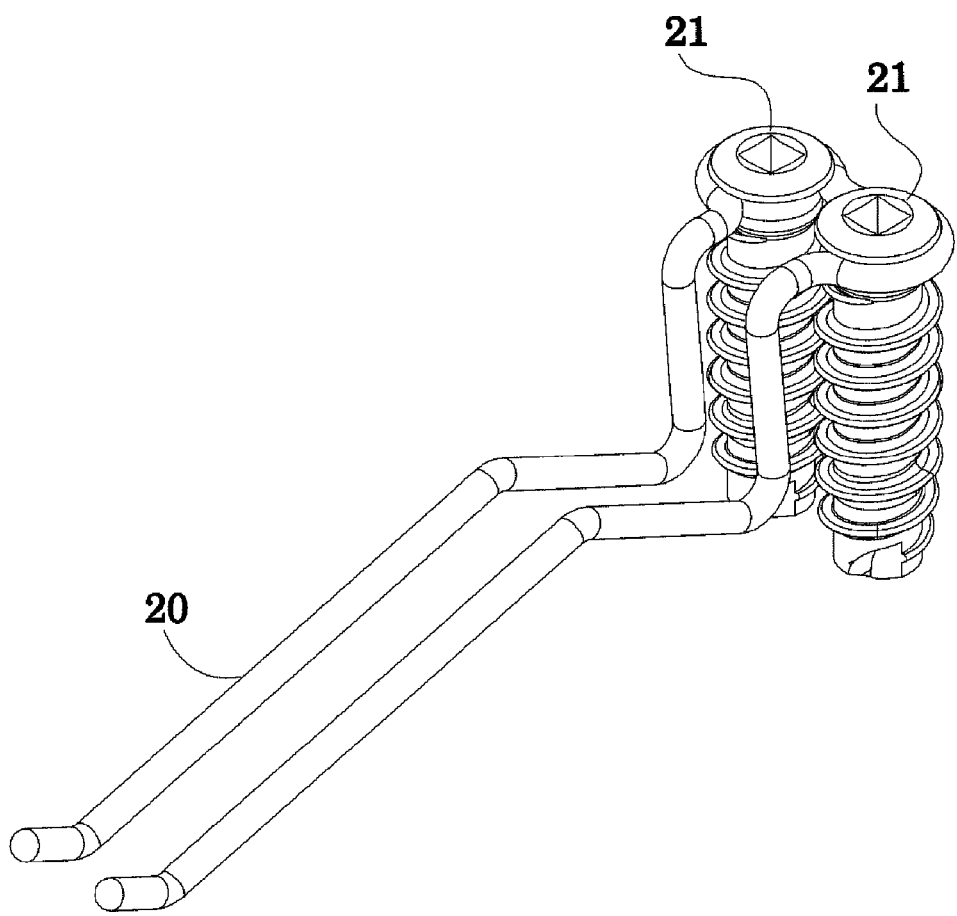
FIG. 6 illustrates a perspective view of an embodiment of a bone pin of FIG. 5 with dual locking cortical screws engagingly mating the locking domains.
Figure 7:
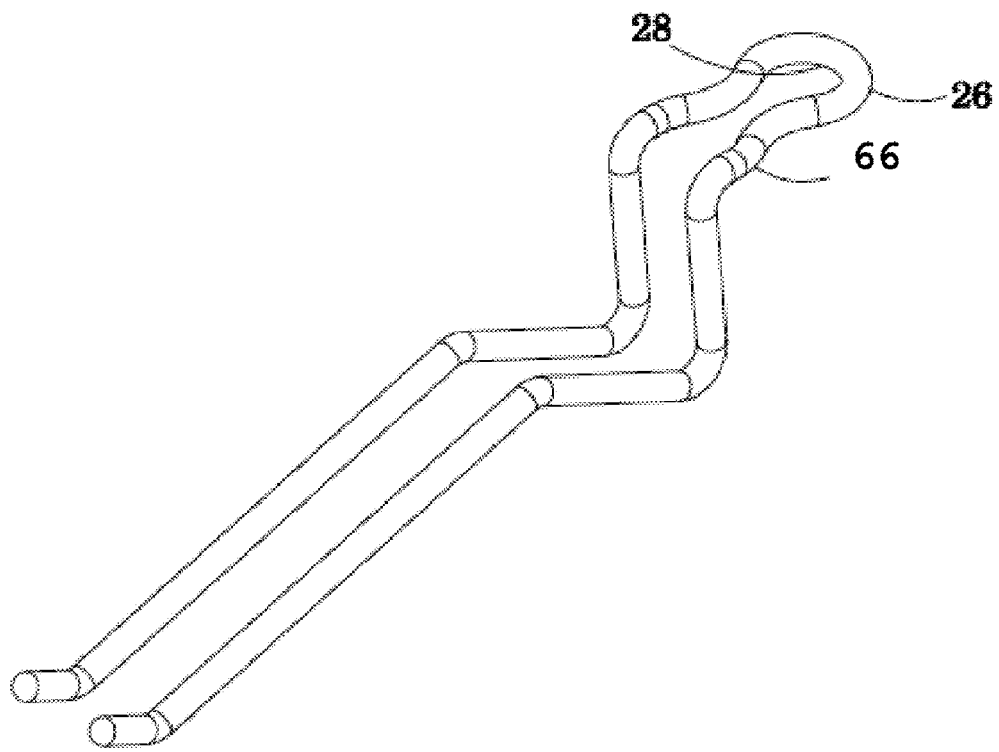
FIG. 7 illustrates a perspective view of an embodiment of a bone pin having a dual prong configuration with dual linear locking domains.
Figure 8:
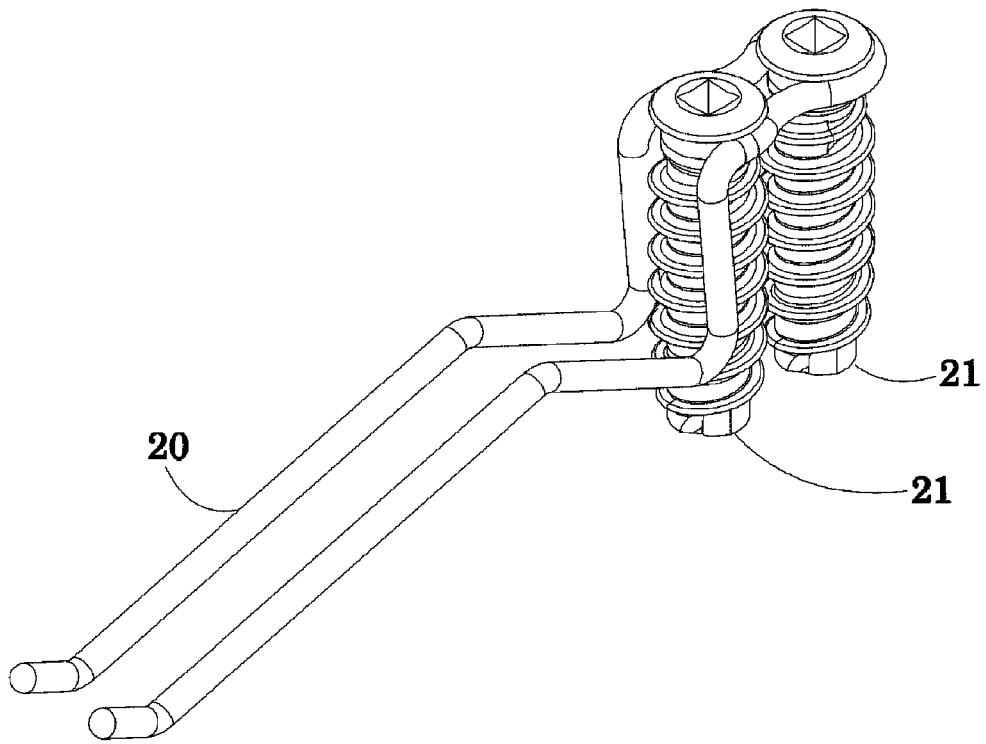
FIG. 8 illustrates a perspective view of a bone pin of FIG. 7 with dual locking cortical screws engagingly mating the locking domains with the mating feature of the screw.
Figure 10:
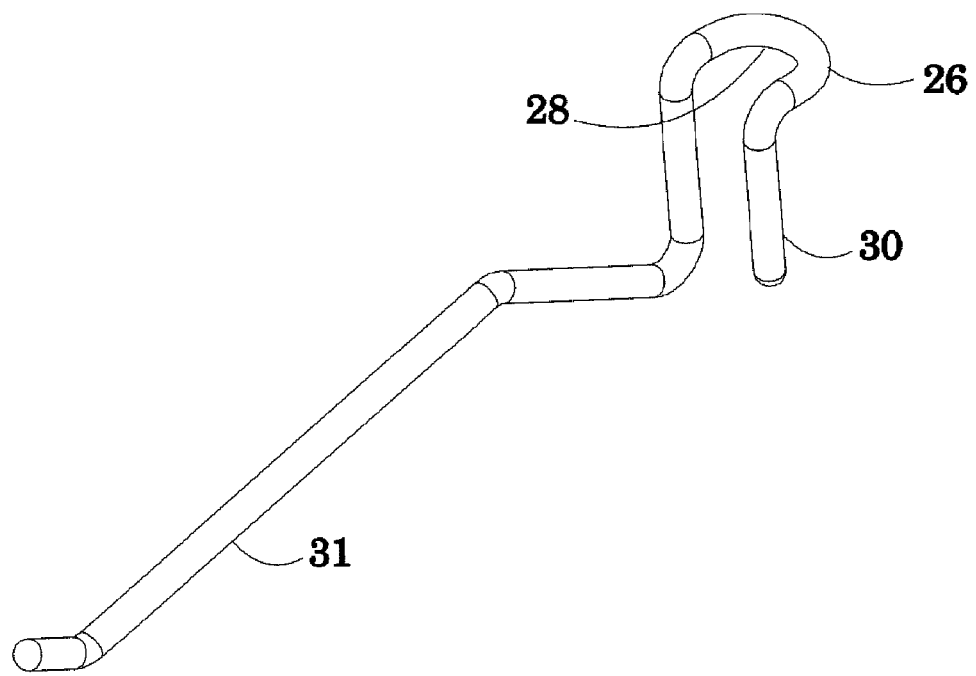
FIG. 10 illustrates a perspective view of a bone pin having a single locking domain and dual prong configuration with varying prong length.

However, pin 20 can be configured in many different shapes and sizes to accommodate any situation. For example, FIG. 1 illustrates a single loop dual prong configuration with prongs 22 and 24 of equal length and shape. FIG. 4 illustrates the embodiment of FIG. 1 showing a locking cortical screw 21 engagingly mating the locking domain. FIGS. 5 and 6 show perspective view of a lateral dual loop configuration 64 with FIG. 6 illustrating screws 21 engagingly mating with the lateral loop 64. FIGS. 7 and 8 show perspective view of a linear dual loop configuration 66, with FIG. 8 illustrating screws 21 engaging mating lateral loop 66. FIG. 10 further illustrates the prong configuration variation with two varying prong lengths-one short and straight 30 and the other prong with an arch 31.

In some embodiments, the prongs have a cylindrical shape, i.e., a round cross-section. The pin profile is not limited to a round cross-section and may also be constructed using any profile e.g. square, hexagon, and triangle. In addition, the contour of the prongs may also take any form pertaining to its particular application. The inner surface of the cylindrical shape in the dual linear loop area would be positioned against the bone surface.

Figure 9:
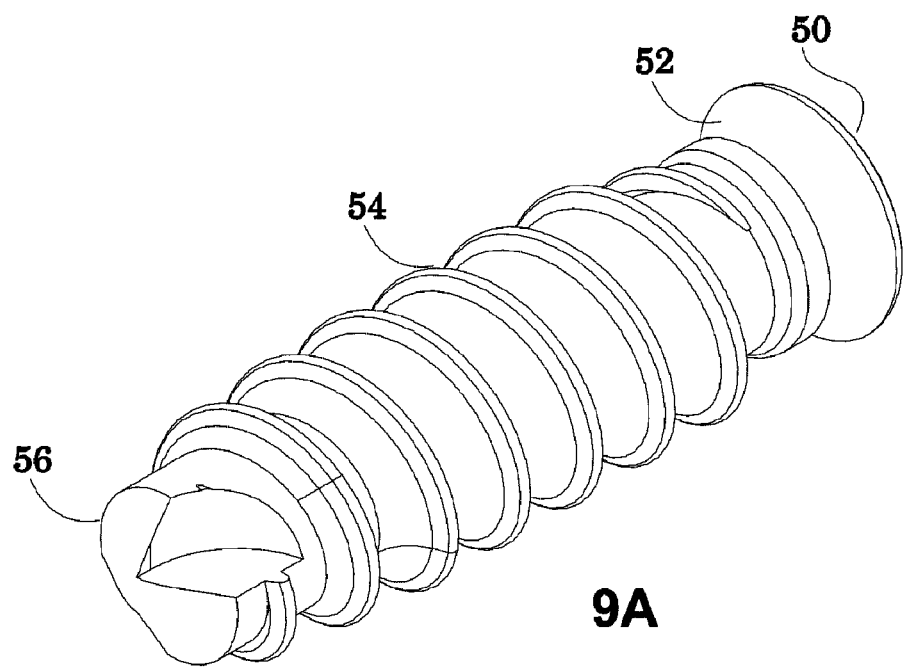
FIGS. 9A and 9B illustrates front and rear perspective views of a locking cortical screw, showing the self-cutting tip, the loop mating groove, and the drive socket.
Figure 9:
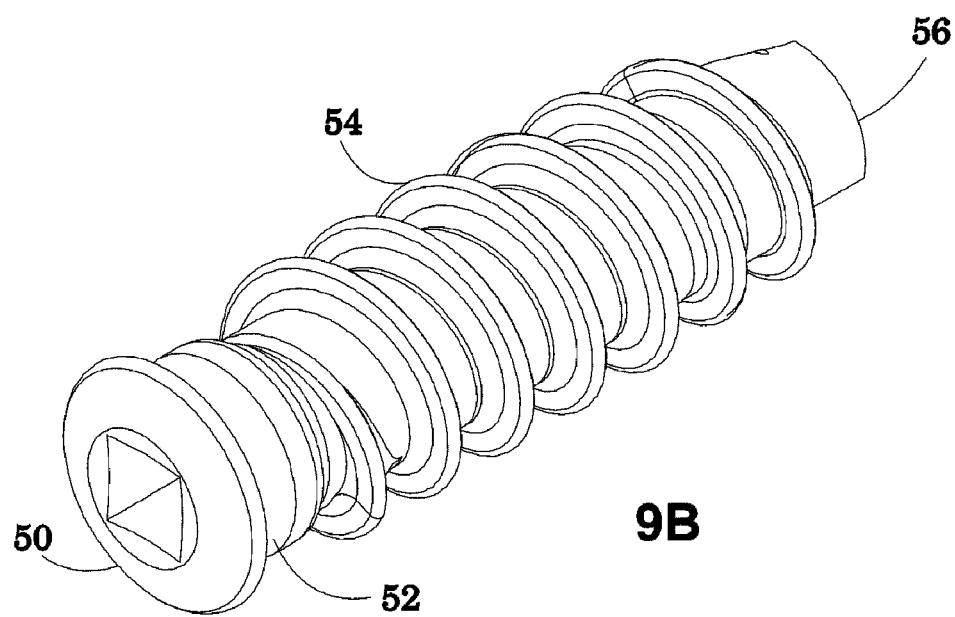

Loop 28 is configured to receive above screw 21 therethrough. Screw 21 is used to anchor dual prong pin 20 to the particular bone segments that require fixation. As shown in FIG. 9, screw 21 has a head region 50 respectively at a proximal end 52. Screw 21, which includes a threaded portion 54, extends from the head region 50 to a distal end 56 of the screw. The locking cortical screw engages the loop with the mating feature of the screw.

Figures 13, 13A, 13B, 13C, 13D:
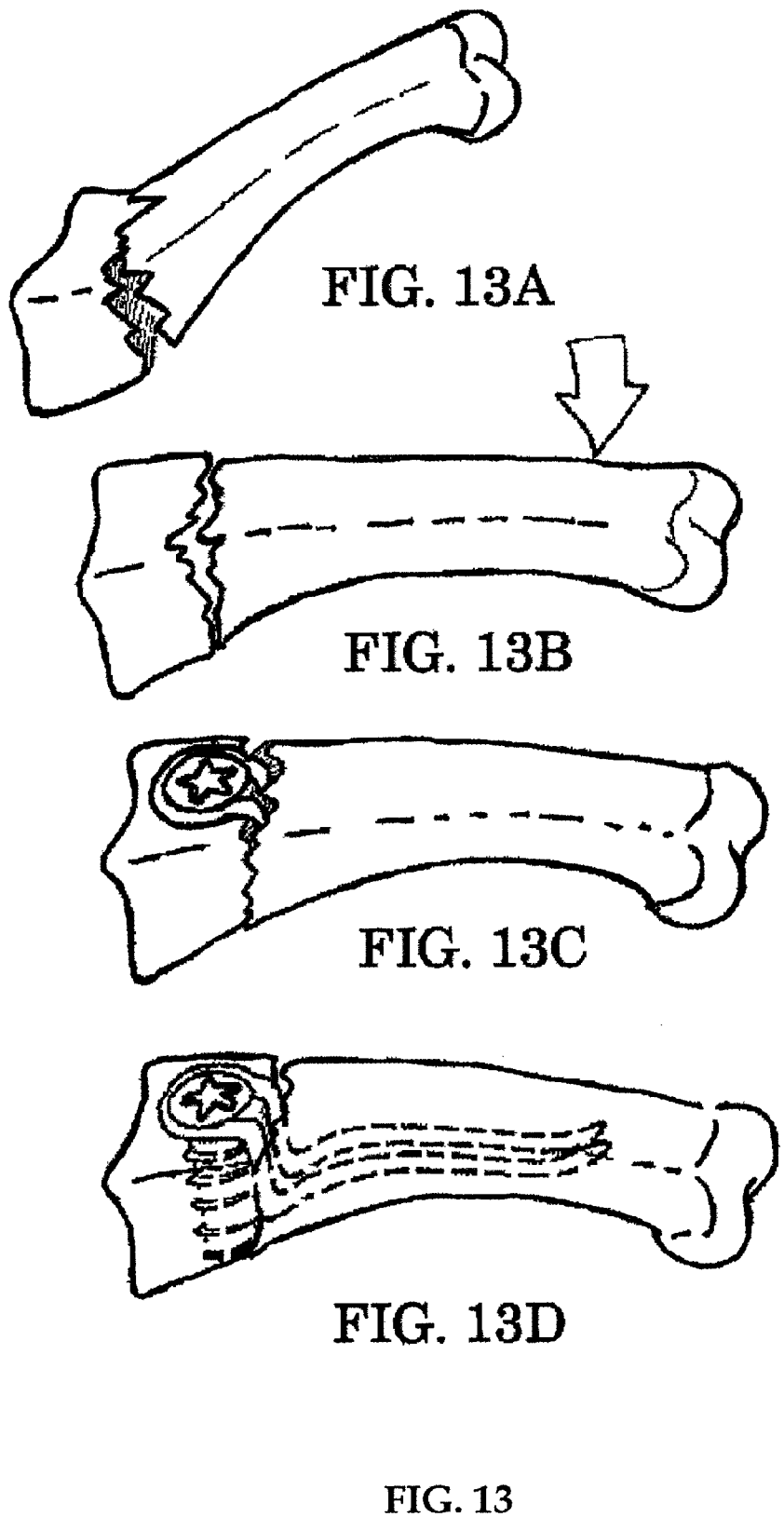
FIGS. 13A, 13B, 13C and 13D illustrate the placement of a bone pin system in accordance with the invention at a fracture site.

To facilitate insertion, the threaded screws can be self-tapping screws. The screw can also be self-drilling screw or pre-drilled with the aide of a drill guide. Additionally, the screws can be cannulated for insertion of a guide wire to guide screw placement. The length of the individual screw shaft can be selected for the particular application. FIG. 13 illustrates the placement of pin 20 in accordance with the invention at a fracture site.

That two prongs can be mated to the screw provides additional fixation to bone because a screw, oriented into the bone, will offer much more resistance to pull out than any existing configuration. Torsional resistance is also theoretically greatly increased.

Figure 11:
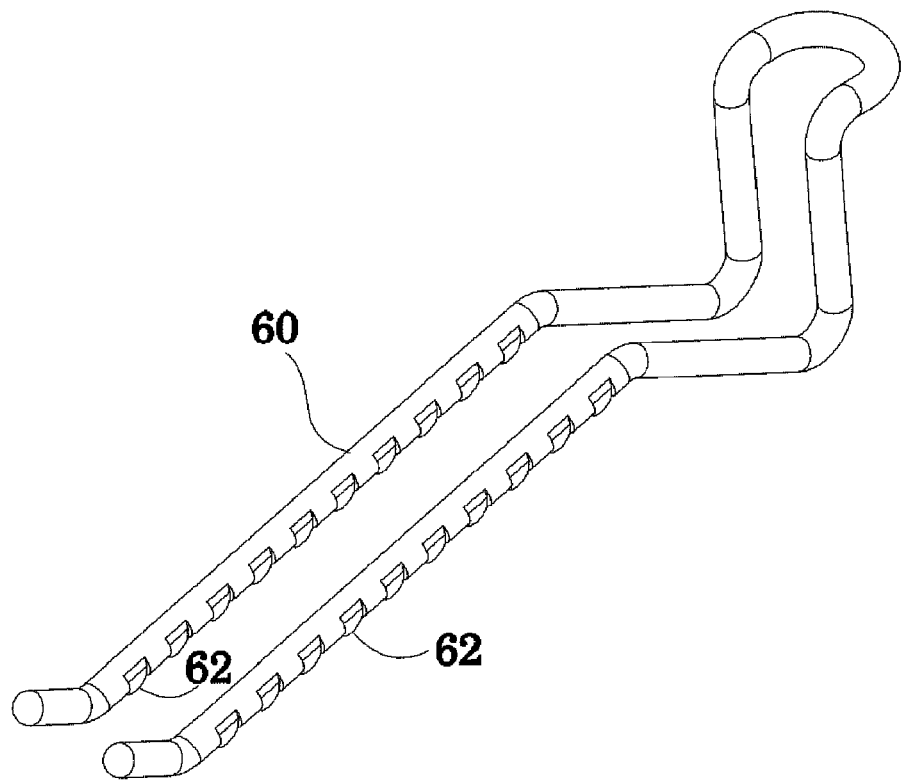
FIG. 11 illustrates a perspective view of a bone pin having dual prong configuration and single locking domain with a series of barbs along the shank portion of the prongs.
Figure 12:
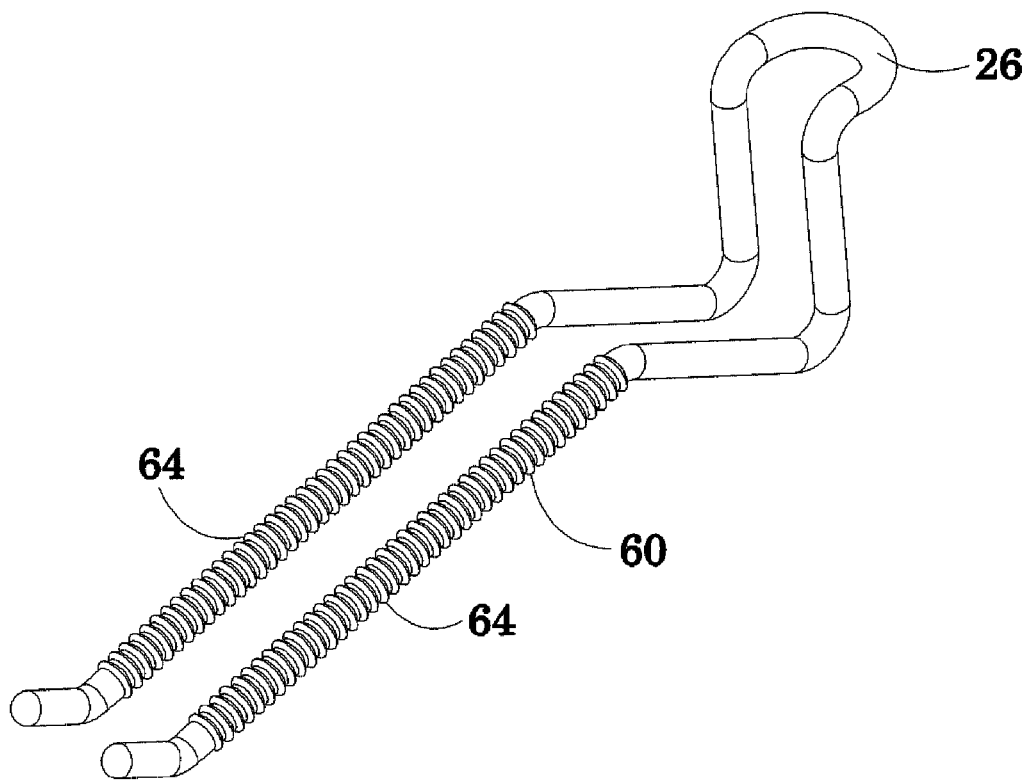
FIG. 12 illustrates a perspective view of a bone pin having a dual prong configuration and a single locking domain a series of ringed protrusions along the shank portion of the prongs.

Prongs 22, 24 may have a shank portion 60. In an embodiment, prongs 22, 24 have barbs 62 disposed along shank 60, as shown in FIG. 11. In another embodiment, as shown in FIG. 12, two prong pin 20 in accordance with embodiments of the invention has a retaining feature configuration located on the distal portion of the prongs. This retaining configuration can take the form of raised ring or protrusions 64 on the underside of the prongs. These configuration variations help increase the gripping power of the prongs thus preventing separation of the fracture.

As described herein, the dual prong pin may be sized and configured for particular application, thus allowing the pin to be applied to the tibia, femur, humerus, forearm bone, and other bones with which the invention may be used.

One of ordinary skill in the art will know and appreciate that dual prong pin 20 may be provided with other types and configurations of prongs in addition to the dual prongs as illustrated. For example, dual prong pin 20 may be provided with substantially varied configurations to its prongs and mounting, with prongs consisting of varied shapes, configurations, and mountings on a single device as shown in the drawings, or any other type of configuration known to one of ordinary skill in the art, e.g., one of the two prongs could be smooth with the other having a barbed feature.

In practice, the two prong device is designed to "snap" in place at the fracture site. In various embodiments, the second bend of the prongs after the locking loop in the sagittal plane is intended to secure the dorsal cortex of the bone at the fracture site, thus providing a first point of fixation. The third bend of the device in the sagittal plane works to provide the second point of support for the device in the proximal fracture end. The third and gentler bend in the sagittal plane works to provide the first point of fixation to the distal fracture fragment across the fracture site. A second point of support to the fragment across the fracture site is provided by the two long prongs of the device. Basically four points of fixation are achieved, two in the proximal fracture fragment and two in the distal fracture fragment.

The invention also provides a method of fixating bone fractures. The method includes positioning a dual prong pin having, e.g., a loop, at the site of a fracture, and inserting bone screw through the loop of the dual prong pin, thus locking the pin and fragments to fixate the fracture. FIG. 13 illustrates the placement of the bone fixation system at the site of the fracture.

The foregoing description is considered as illustrative only of the principles of the invention. Further, since numerous modifications and changes may readily occur to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A bone fixation system for aiding reduction of a fractured bone, said bone fixation system comprising:
 a bone pin adapted to support portions of the fractured bone, said bone pin having a first prong, a second prong, a central portion, and a mid-longitudinal axis extending through said central portion and between said first and second prongs, said central portion including a first end, a second end, and at least one arcuate portion, said at least one arcuate portion defining at least in part at least one opening for receiving at least one bone screw, said at least one arcuate portion being adapted to engage a portion of said at least one bone screw, said at least one arcuate portion extending around at least 180 degrees and having a first radius, said at least one opening comprising a first opening and a second opening, each of said first and second openings defined by portions of two of a first arcuate portion, a second arcuate portion, and a third arcuate portion of said at least one arcuate portion, said first opening adapted to receive a first bone screw of said at least one bone screw and said second opening adapted to receive a second bone screw of said at least one bone screw, said first opening and said second openings each having a center, said centers of said first and second openings being provided on opposite sides of the mid-longitudinal axis of said bone pin, said first prong extending outwardly from said first end of said central portion and said second prong extending outwardly from said second end of said central portion, said first and second prongs being symmetrical about a first plane extending through the mid-longitudinal axis and bisecting said central portion, said first and second prongs each including a substantially straight portion and a bone engaging portion adapted to contact the portions of the fractured bone; and
 said at least one bone screw having a proximal end, a distal end opposite said proximal end, a head portion proximate said proximal end, and a shaft portion extending from said head portion to said distal end, said head portion having a first surface oriented toward said distal end, said first surface being adapted to engage said at least one arcuate portion of said bone pin, said head portion having a second radius, and said shaft portion having a third radius adjacent said head portion, wherein said first radius of said at least one arcuate portion is less than said second radius and greater than said third radius.

2. The system of claim 1, wherein said centers of said first and second openings are offset from one another along a line parallel to the mid-longitudinal axis of said bone pin.

3. The system of claim 1, wherein said centers of said first and second openings are offset from one another along a line transverse to the mid-longitudinal axis of said bone pin.

4. A bone fixation system for aiding reduction of a fractured bone, said bone fixation system comprising:
 a bone pin adapted to support portions of the fractured bone, said bone pin having a first prong, a second prong, a central portion, and a mid-longitudinal axis extending through said central portion and between said first and second prongs, said central portion including a first end, a second end, and at least one arcuate portion, said at least one arcuate portion defining at least in part at least one opening for receiving at least one bone screw, said at least one arcuate portion being adapted to engage a portion of said at least one bone screw, said at least one arcuate portion extending around at least 180 degrees and having a first radius, said at least one opening comprising a first opening and a second opening, each of said first and second openings defined by portions of two of a first arcuate portion, a second arcuate portion, and a third arcuate portion of said at least one arcuate portion, said first opening adapted to receive a first bone screw of said at least one bone screw and said second opening adapted to receive a second bone screw of said at least one bone screw, said first opening and said second openings each having a center, said first arcuate portion and said second arcuate portion define a first lobe and a portion of said first opening, and said second arcuate portion and said third arcuate portion define a second lobe and a portion of said second opening, said first and second lobes being provided on opposite sides of the mid-longitudinal axis of said bone pin, said first prong extending outwardly from said first end of said central portion and said second prong extending outwardly from said second end of said central portion, said first and second prongs being symmetrical about a first plane extending through the mid-longitudinal axis and bisecting said central portion, said first and second prongs each including a substantially straight portion and a bone engaging portion adapted to contact the portions of the fractured bone; and said at least one bone screw having a proximal end, a distal end opposite said proximal end, a head portion proximate said proximal end, and a shaft portion extending from said head portion to said distal end, said head portion having a first surface oriented toward said distal end, said first surface being adapted to engage said at least one arcuate portion of said bone pin, said head portion having a second radius, and said shaft portion having a third radius adjacent said head portion, wherein said first radius of said at least one arcuate portion is less than said second radius and greater than said third radius.

5. The system of claim 4, wherein said first arcuate portion and said third arcuate portion extend around said centers of said first and second openings, respectively, at least 180 degrees.

6. The system of claim 5, wherein said second arcuate portion extends between said first and third arcuate portions.

7. The system of claim 1, wherein said first arcuate portion defines a portion of said first opening, and said second and third arcuate portions define a portion of said second opening.

8. The system of claim 7, wherein said first arcuate portion extends around said center of said first opening more than 180 degrees.

9. The system of claim 1, wherein said first prong extends in a second plane and said second prong extends in a third plane, said second and third planes being parallel to one another.

10. The system of claim 9, wherein said first and second prongs each include a first portion and a second portion, said first portions and second portions being at angled relationships with one another.

11. A bone pin, comprising: a substantially U-shaped member having a central region, a first prong extending from the central region and a second prong extending from the central region, opposite and parallel from the first prong, the central region configured to receive and mate with one or more bone screws, wherein the first and second prong each are substantially arched, each include a first arcuate portion extending from the central region, a first straight line portion extending from the first arcuate portion, substantially perpendicular to the plane of the central region, a second arcuate portion extending from the first straight line portion, a second straight line portion extending from the second arcuate portion and at an angle from the first straight line portion, a third arcuate portion extending from the second straight line portion, and an end portion which is in a straight line and at an angle from the second straight line portion.

12. The pin of claim 11, wherein the first and second prong are equal in length.

13. The pin of claim 11, wherein the first and second prongs are unequal in length.

14. The pin of claim 11, wherein the central region is an arcuate portion defining a single screw locking member.

15. The pin of claim 14, wherein the single screw locking member is an arcuate loop lying a horizontal plane.

16. The pin of claim 11, wherein the central region is two arcuate portions defining a dual screw locking member.

17. The pin of claim 16, wherein the dual screw locking member has a first and second arcuate loops.

18. The pin of claim 17, wherein the second arcuate loop lies laterally in the horizontal plane of the first arcuate loop.

19. The pin of claim 17, wherein the second arcuate loop lies linearly in the horizontal plane of the first arcuate loop.

20. The pin of claim 17, wherein the second arcuate loop comprises arcuate portions of the first and second prongs, the portions being opposite each other and oppositely contoured to each other.

21. The pin of claim 11, wherein the first straight line portions of the first and second prongs are perpendicular to the plane of the central region.

22. A bone pin, comprising: a substantially U-shaped member having a central region, a first prong extending from the central region and a second prong extending from the central region, opposite and parallel from the first prong, the central region configured to receive and mate with one or more bone screws, wherein the central region is two arcuate portions defining a dual screw locking member, the dual screw locking member has a first and second arcuate loops, and the second arcuate loop lies laterally in a horizontal plane of the first arcuate loop, the first prong being substantially arched, the first prong including a first arcuate portion extending from the central region, a first straight line portion extending from the first arcuate portion, substantially perpendicular to the plane of the central region, a second arcuate portion extending from the first straight line portion, a second straight line portion extending from the second arcuate portion and at an angle from the first straight line portion, and a third arcuate portion extending from the second straight line portion.

23. The pin of claim 22, wherein the first and second prong are equal in length.

24. The pin of claim 22, wherein the first and second prongs are unequal in length.

* * * * *